United States Patent [19]

Newman

[11] 3,993,054

[45] Nov. 23, 1976

[54] THERAPEUTIC LAVAGE

[75] Inventor: Gordon Arthur Newman, Schoolcraft Township, Kalamazoo County, Mich.

[73] Assignee: Stryker Corporation, Kalamazoo, Mich.

[22] Filed: June 19, 1975

[21] Appl. No.: 588,495

[52] U.S. Cl. .................................. 128/66; 128/230
[51] Int. Cl.² ........................................ A61H 9/00
[58] Field of Search ................ 128/66, 230, 214 F, 128/DIG. 12; 417/476, 477

[56] References Cited
UNITED STATES PATENTS

| 320,888 | 6/1885 | Ruffel .................................. 417/476 |
| 3,288,239 | 6/1975 | Rubinstein ....................... 128/214 F |
| 3,542,491 | 11/1970 | Newman .......................... 417/477 X |
| 3,799,702 | 3/1974 | Weishaar ..................... 128/DIG. 12 |
| 3,910,266 | 10/1975 | Kawase ................................ 128/66 |

*Primary Examiner*—Lawrence W. Trapp
*Attorney, Agent, or Firm*—Woodhams, Blanchard and Flynn

[57] ABSTRACT

A housing having a motor mounted therein with the shaft thereof projecting through an opening in one sidewall of the housing. A partially cylindrical wall is mounted upon the sidewall substantially concentric with the rotational axis of the motor, and a rotor is eccentrically mounted upon the shaft for rotation relative thereto. A resiliently flexible tube is disposed between the rotor and the wall, whereby to produce what is called a peristaltic type of pumping action with each rotation of the shaft. Thus, a liquid disposed within the tube is urged intermittently to move through the tube in a pulsating manner. One end of the tube is connected to a source of liquid and the other end is connected to a nozzle having a manually-operable flow control device thereon.

9 Claims, 11 Drawing Figures

THERAPEUTIC LAVAGE

FIELD OF THE INVENTION

This invention relates in general to an apparatus, referred to as a therapeutic lavage, for producing a pulsating flow of liquid from a source thereof through a tube for irrigating or washing a wound or incision in flesh, as during the performance of surgery.

A device of this general type, but specifically utilized for oral hygiene, is disclosed in U.S. Pat. No. 3 227 158, issued Jan. 4, 1966.

BACKGROUND OF THE INVENTION

In the treatment of tissue, both externally and within an incision or wound, it has been found that a controllable pulsating stream of liquid provides a therapeutic action which is desirable in promoting prompt and correct healing. Thus, devices, such as the one shown in the above-mentioned patent, have been developed broadly for this purpose. However, certain problems have developed in the use of this type of apparatus, particularly where contamination of the apparatus is likely or even possible as the result of such use. That is, it has heretofore been difficult and inconvenient to sterilize existing equipment for this purpose after, for example, use thereof in irrigating an infected wound or an incision in infectious tissue. Also, existing equipment for this purpose is complicated, hence expensive in construction and it lacks a simple, inexpensive means for controlling the flow of the pulsated liquid from the apparatus.

Accordingly, a primary object of this invention is the provision of a therapeutic lavage capable of producing a manually controllable, pulsating stream of liquid through a tube which can be quickly and easily removed from the pulse-creating mechanism so that only the tube means and its flow control device need sterilization and/or replacement. That is, most of the apparatus, which includes the parts thereof which produce the pulsating flow of liquid through the tube means, do not require sterilization after normal use.

Other objects and purposes of this invention will become apparent to persons familiar with this type of equipment upon reading the following specification and examining the accompanying drawings.

Figure 1:
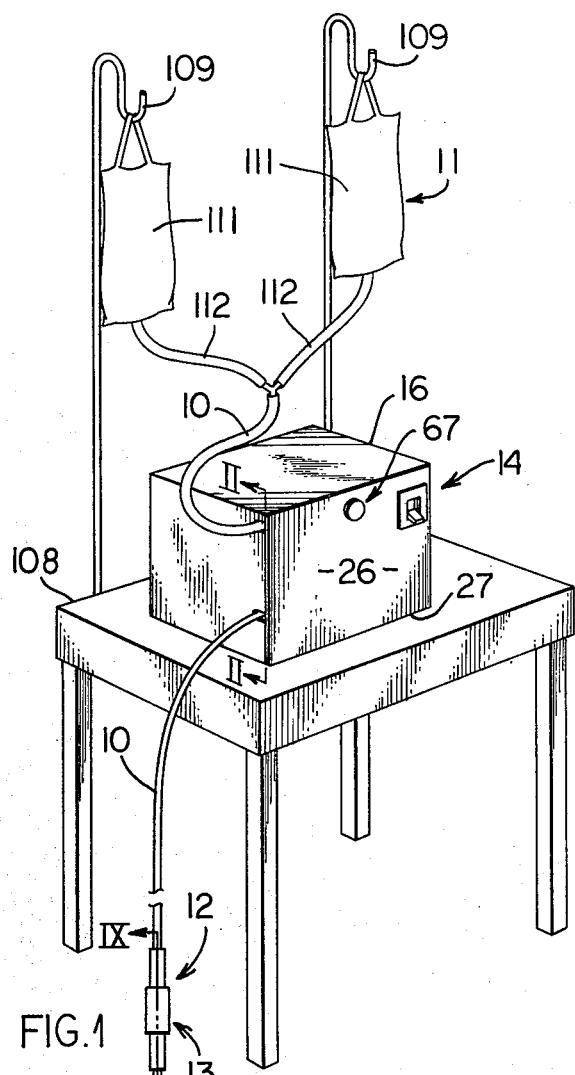
FIG. 1 illustrates the apparatus of the invention disposed upon a support having means for holding one or more containers containing a supply of liquid which is furnished to the apparatus.

For convenience in description, the terms "upper", "lower", "front", "rear" and words of similar import will have reference to the apparatus as appearing in FIG. 1 which shows the front, left and top sides of the apparatus. The terms "inner", "outer" and derivatives thereof will have reference to the geometric center of said apparatus and major components thereof.

SUMMARY OF THE INVENTION

The objects and purposes of the invention, including those set forth above, have been met by providing a therapeutic lavage having a cabinet with a motor and a pump mounted therein. Motor shaft means projects through an opening in the front wall of the cabinet and eccentrically supports thereon a pump rotor means for rotation relative to the shaft means. Pump housing means, which is mounted upon the outside of said front wall, and is independent of the motor, has wall means that surround at least a substantial portion of the rotor means and is spaced radially therefrom. A one-piece elongated tube is disposed between the rotor means and the wall means and the ends thereof extend outwardly from the cabinet. When the shaft means is rotated, the rotor means coacts with the wall means in a peristaltic type pumping action which causes liquid in the tube to be urged therethrough in a pulsating manner. One end of the tube is connected to a source of liquid and the other end of the tube is furnished with a nozzle having a flow control device thereon.

DETAILED DESCRIPTION

In a preferred embodiment of the invention, as illustrated in FIG. 1, the therapeutic lavage of the invention is comprised of a one-piece, liquid conveying, resiliently flexible tube 10 connected at one end to a source 11 of liquid and at its other end to a discharge nozzle 12 having manually controllable valve means 13 for restricting the flow of liquid through said nozzle. The tube 10 extends through pump means 14 within the cabinet 16 (FIG. 2) so that said pump means can generate a pulsating flow of liquid through said tube.

The cabinet 16 has a front wall 17, top wall 18, left sidewall 19, right sidewall 20, bottom wall 21 and rear wall 22. The front wall 17 (FIG. 7) is recessed from the front edges of the top, bottom and sidewalls of the cabinet 16 to provide a front compartment 24 which is normally covered by a door 26 hingedly mounted along its lower edge by a hinge 27 upon the front edge of the bottom wall 21.

Figure 3:
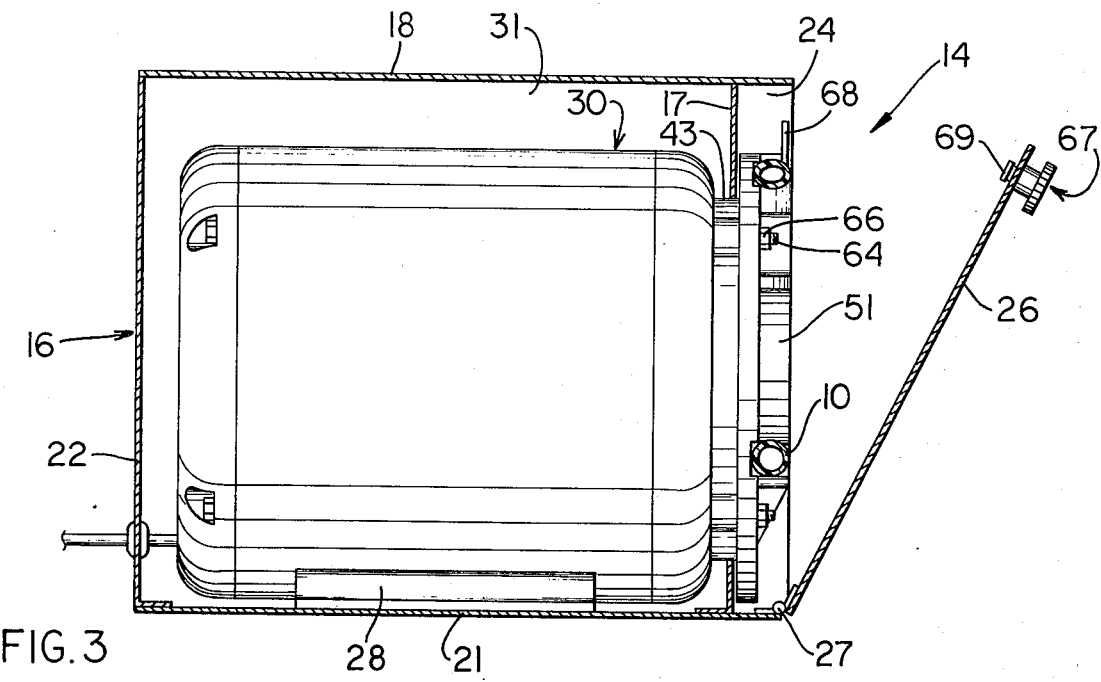
FIG. 3 is a sectional view along line III—III in FIG. 2.

A motor 30 (FIG. 3) is supported by mounting feet 28 upon the bottom wall 21 within the rear compartment 31 of the housing 16 between the front and rear walls thereof. The motor 30 is enclosed within its own housing and has a shaft 32 which extends frontwardly therefrom toward an enlarged opening 33 in the front wall 17. The shaft 32 is rotatably supported near its front end by bearing means 34 mounted within the front end wall 36 of the motor housing. A portion 37 of said shaft 32 is adapted for threaded reception into a threaded recess 38 concentrically disposed within the rear end of a crankshaft 41. An eccentric crank pin 42 is rigidly secured to the front end of the crankshaft 41 and is disposed within the front chamber 24.

The pump means 14 (FIG. 2), which is the peristaltic type, includes a small annular pump housing 43 which is independent of the motor housing and cabinet and has a radially inwardly facing wall 44, a part 46 thereof defining a portion of a cylinder coaxial with the motor shaft 32. The wall 44 (FIG. 2) also includes straight portions 47 and 48 which diverge away from the cylindrical part 46 approximately at a 45° angle. The rear wall 40 of the pump housing 43 has a circular opening 45 through which the crankshaft 41 extends. The door 26 closes and defines the front side of the pump housing 43.

Figure 7:
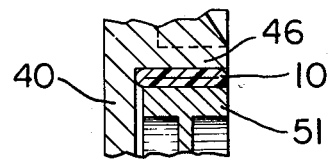
FIG. 7 is a fragmentary sectional view taken along the line VII—VII in FIG. 5.
Figure 4:
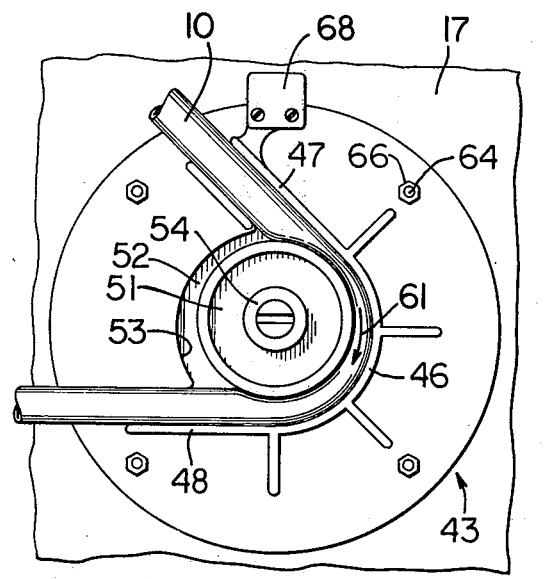
FIGS. 4 and 5 are fragments of FIG. 2 illustrating parts thereof in different relative positions.
Figure 5:
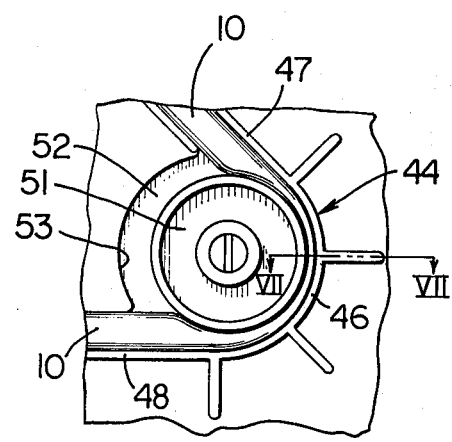

A substantially cylindrical rotor 51 is disposed within a pump chamber 52 which is substantially defined by the wall part 46 and the opposing wall fragment 53 which also defines a portion of the cylinder that defines the inner surface of the wall part 46. The rotor 51 has a hub 54 with a smooth central and coaxial opening 56 in which bearing means 57 is disposed for snug reception of the crank pin 42 therewithin. Thus, the rotor 51 is rotatably supported upon the crank pin 42 by the bearing means 57. As the rotor 51 is rotated with the crank pin 42 around the axis of the shaft 32, the peripheral surface 58 of the rotor 51 moves toward and away from the wall part 46 with a rolling motion through a distance equal to the eccentricity or throw of the crank pin 42. The tube 10 extends through the pump chamber 52 between the peripheral surface 58 of the rotor 51 and the wall 44 of the pump housing 43. Thus, as consecutively shown in FIGS. 2, 4 and 5, the tube 10 is pinched, as shown in FIG. 7, progressively from the top of the pump chamber 52 around to the bottom of the pump chamber 52 with each rotation of the motor shaft 32, thereby urging or pinching the liquid within that portion of the tube in the direction of the arrow 61 in FIG. 4.

The pump housing 43 has a cylindrical flange 62 (FIG. 6) projecting rearwardly from the rear wall 40 thereof, which flange 62 is preferably snugly received into and through the opening 33 in the front wall 17 of the cabinet 16. The cylindrical flange 62 snugly engages the front face of the front wall 36 of the motor 30. Said pump housing 43 has a plurality of openings, one of which is shown in broken lines at 63 in FIG. 6, through which studs 64 are received. The rearward ends of studs 64 are firmly anchored in the front wall 36 of the motor and they are threadably engaged by nuts 66 for firmly holding said pump housing 43 in place.

The upper end of the pump housing 43 has a catch 67 (FIG. 8) secured thereto and extending upwardly therefrom adjacent the door 26. The catch 67 is comprised of a finger 69 secured to a pin 72 which rotatably extends through the door 26 and is secured to a manually turnable knob 73 for rotating the pin 72 and thereby the finger 69 into and out of positions of engagement with a latch 68 which is secured to the pump housing 43.

Figure 9:
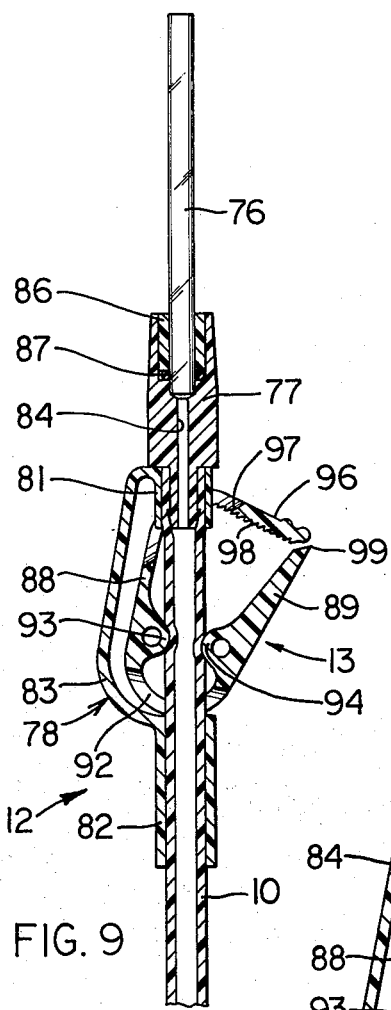
FIG. 9 is an enlarged sectional view of the flow control valve as taken along the line IX—IX in FIG. 1.
Figure 10:
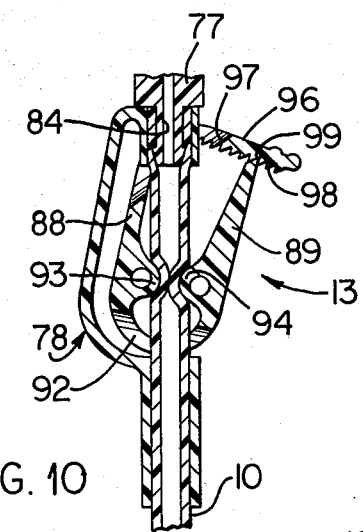
FIG. 10 is a sectional view similar to FIG. 9 and showing the valve in a closed position.

The nozzle 12 (FIG. 9) has a discharge pipe 76 which is relatively stiff, and is sleeved within a cylindrical connector 77 which is in turn connected to the outlet end of the tube 10. A brace 78, which also serves as a guard for one side of the valve means 13, has a pair of coaxial sleeves 81 and 82 which are rigidly secured to the opposite ends of a sidewardly projecting bridge 83. The upper sleeve 81 surrounds and tightly embraces the upper end (FIG. 9) of the tube 10, thereby holding it firmly on the connector 77. The lower sleeve 82 surrounds and snugly embraces the tube 10 in a region spaced downwardly from the sleeve 81. The tube 10 is resiliently flexible so that it can be compressed by the valve means 13, as shown in FIG. 10, to completely block the flow of liquid through said tube 10.

The cylindrical connector 77 has a central opening 84 which is enlarged at its upper end to receive a cylindrical insert 86, which snugly surrounds the lower end of pipe 76. The insert 86 is tightly held in the connector 77 and has its lower end compressing an O-ring 87 against the adjacent portion of the connector 77 to provide a liquid-tight seal between the connector 77 and the pipe 76.

Figure 8:
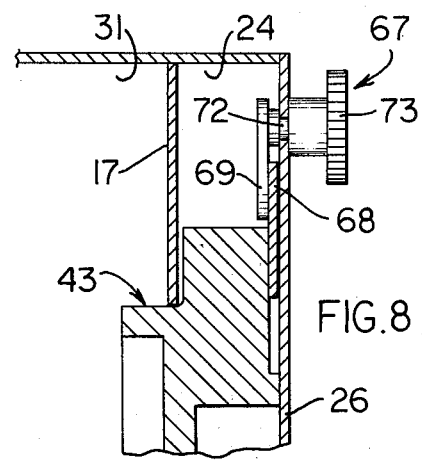
FIG. 8 is an enlarged, fragmentary sectional view taken along the line VII—VII of FIG. 2.

The valve means 13 has a pair of levers 88 and 89 which are hingedly connected at corresponding ends thereof to a pair of spaced hinge elements, one of which is shown at 92 in FIG. 8, which hinge elements are disposed on opposite sides of the pipe 76 and are sufficiently elongated to permit pivotal movement of the levers 88 and 89 as discussed hereinafter. The levers 88 and 89 have directly opposed projections 93 and 94 which extend toward each other and are engageable with opposite sides of the pipe 76 for effecting compression thereof. An integral flange 96 is secured to the upper end of the lever 88 and extends toward the upper end of the lever 89. Said flange 96 and the adjacent portion of the upper end of the lever 88 are provided with a single opening 97 through which the upper end of the pipe 76 and the sleeve 81 freely extend.

The lower surface of the flange 96 is provided with a plurality of closely spaced transverse grooves 98 in which the chisel-shaped upper edge 99 of the lever 89 is removably receivable for releasably holding the lever 89 in a selected position with respect to the lever 88 and thereby controlling the amount of constriction created by the projections 93 and 94 in the pipe 76. The constricting effect can be immediately eliminated by merely lifting the rightward end of the flange 96 away from the upper edge of the lever 89, whereby the flexibility of the hinge elements 92 returns the lever 89 from its FIG. 10 position, for example, to its FIG. 9 position.

Figure 2:
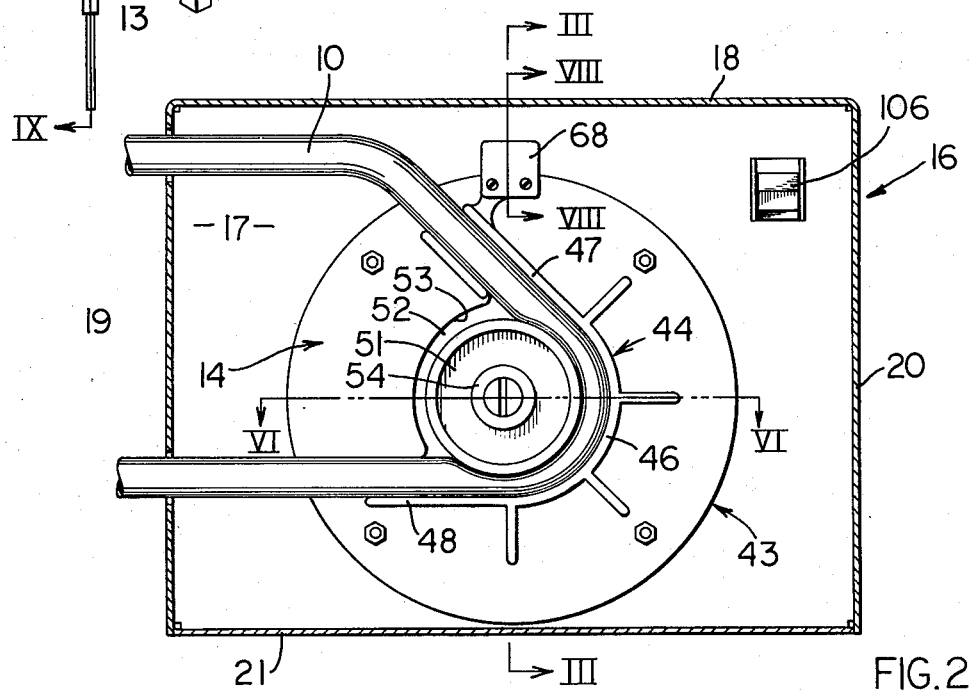
FIG. 2 is a sectional view taken along the line II—II in FIG. 1.
Figure 11:
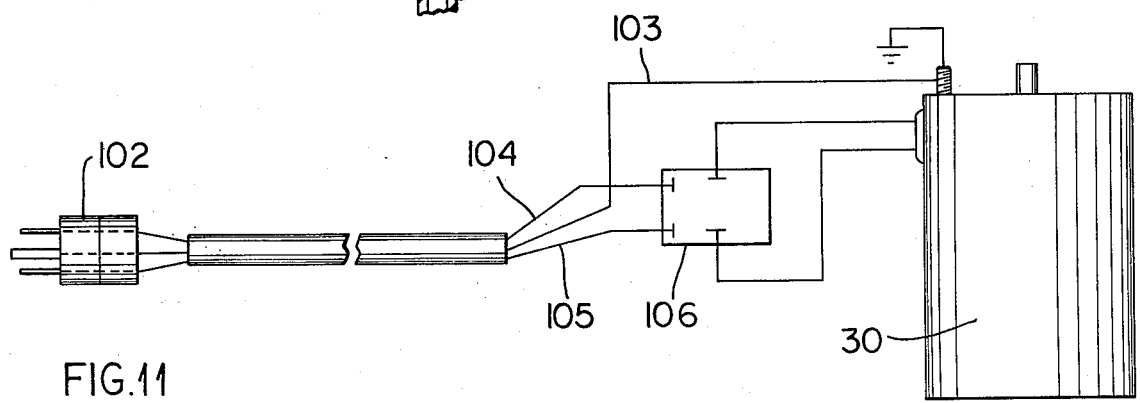
FIG. 11 is a wiring diagram for said apparatus.

FIG. 11 shows a diagram of the electrical circuit whereby the motor 30 is energized. The plug 102 is connectible to any convenient supply of potential, such as 110 volts 60 cycle, and for safety sake, is provided with a ground wire 103. The supply lines 104 and 105 are connected through a double pole single throw switch 106 which, as shown in FIG. 2, is mounted on the front wall 17 of the cabinet 16 so that its actuator extends through an appropriate opening in the door 26.

The cabinet 16 may be placed upon a bench 108 which also supports one or more upright hangers 109 from which liquid supply containers 111 are suspended. The upper or inlet end of the tube 10 is connected by conventional means to the outlet conduits 112 on the containers 111.

OPERATION

Although the operation of the therapeutic lavage of the invention will be apparent to persons skilled in this art upon reading the foregoing descriptive material, a brief summary thereof will be set forth hereinafter.

Figure 6:
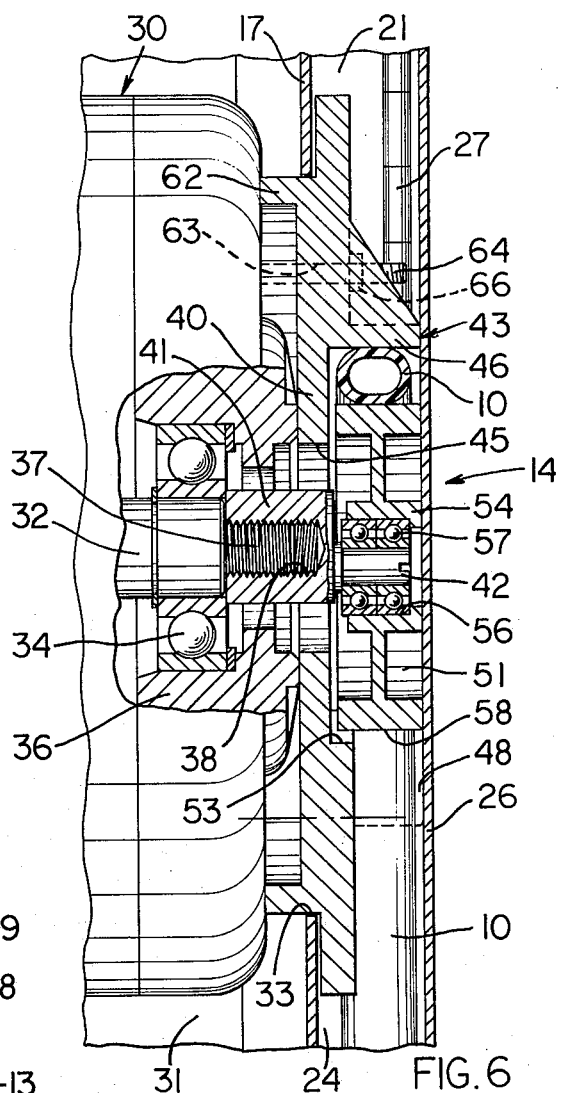
FIG. 6 is an enlarged, fragmentary sectional view taken along the line VI—VI in FIG. 2.

The motor 30 (FIG. 10) is energized by first inserting the plug 102 into a suitable receptacle and then closing the switch 106. The rotation of the motor 30 causes an orbital displacement of the rotor 51, which in turn causes compression and release of that part of the tube 10 between the rotor 51 and the wall part 46 with each rotation of the motor 30. The compression as illustrated sequentially in FIGS. 2, 4 and 5 will cause a milking of the involved portion of the tube whereby the liquid therein is moved therethrough in the direction of the arrow 61. However, since the rotor 51 can completely collapse the tube 10, as shown in FIG. 6, against the wall part 46, the movement of the liquid through the tube 10 will be in spaced intervals. Thus, when the motor is rotated at its normal speed of approximately 1140 rpm, the liquid will be ejected from the discharge pipe 76 in a pulsating flow. The amount of such flow of liquid is controlled by the valve means 13 and, more particularly, the position of the lever 89 relative to the position of the lever 88, which position can be held by engagement between the flange 96 and the upper edge 99 of the lever 89.

The flow of liquid through the discharge pipe 76 can be substantially shut off by the valve means 13 if desired. The result will be that the relatively small amount of fluid which is advanced with each rotation of the motor shaft 32 will be forced into the tube 10. However, since the tube 10 is resiliently flexible, it will merely expand somewhat to take in the excess liquid. However, as soon as the rotor reaches its FIG. 2 position during each cycle of rotation, the liquid compressed within the outlet portion of the tube 10 can again, if needed, flow back upwardly into the inlet portion of the tube 10 with its only obstruction to such flow being the force of gravity. Accordingly, the valve means 13 can effectively serve as both a flow control and a shut-off valve.

Since the tube 10 as connected between the liquid source 11 and the flow control valve 13 is of one piece, it can be quickly removed from the apparatus after use and replaced with a clean tube. The small pump housing 43, by being independent of both the motor 30 and cabinet 16, also simplifies the manufacture, assembly and repair of the apparatus. The motor 30, by being independent of both the cabinet 16 and pump housing 43, can be easily repaired or replaced if necessary.

Because the front bearing 34 (FIG. 6) of the motor 30 supports the crankshaft 41 independently of the pump housing 43, alignment problems are minimized. That is, the only clearance problem between the housing 43, the shaft 41 and the rotor 51 occurs in the region thereof (FIG. 4) where the rotor 51 engages the tube 10. However, since the tube 10 is resiliently flexible, it can tolerate considerable variations in the space between the rotor 51 and housing 43.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An apparatus for effecting a therapeutic lavage, comprising:
   rigid frame means;
   a motor on said frame means and having an output shaft means;
   partially cylindrical wall means mounted upon said frame means near said shaft means and substantially concentric therewith;
   rotor means eccentrically mounted upon said shaft means radially within and spaced from said wall means, the peripheral surface of said rotor means being rotatable with respect to said shaft means, the peripheral surface of said rotor means being movable toward, along and then away from said wall means as said shaft means is rotated;
   resiliently flexible tube means extending along and between the peripheral surface of said rotor means and the adjacent surface of said wall means whereby said tube means is substantially compressed with a rolling motion during each rotation of said shaft means to induce the movement of liquid through said tube means;
   retainer means for releasably holding said tube means in position between said roller means and said wall means;
   manually engageable nozzle means on one end of said tube means, said nozzle means having manually controllable valve means for controlling the flow of liquid therethrough, the other end of said tube means being connected to a source of liquid under pressure;
   said valve means comprising a pair of levers pivotally connected to each other near corresponding ends thereof and having projections extending toward each other at points near to but spaced from said corresponding ends, said projections being on opposite sides of said nozzle means, said levers being movable toward each other whereby said projections compress said nozzle means and thereby obstruct flow of liquid therethrough; and
   arm means secured to the other end of one of said levers and projecting toward the other lever, said arm means having notches in the inner surface thereof engageable with the other end of said other lever for releasably holding said levers in predetermined positions relative to each other.

2. An apparatus according to claim 1, wherein said frame means is a substantially rectangular housing which substantially totally encloses said motor;
   wherein said wall means is rigidly secured to one sidewall of said housing and said shaft means extends through an opening therein, said wall means being mounted on the outer side of said sidewall; and
   wherein said retainer means includes a panel hingedly supported upon said housing and movable into and out of a releasably held position substantially parallel with said sidewall and adjacent said rotor means.

3. An apparatus for effecting a therapeutic lavage, comprising:
   housing means defining therein a substantially closed compartment, said housing means including top and bottom walls interconnected by a pair of sidewalls, said housing means further including front and rear walls connected to the aforesaid walls for defining said compartment between said walls, said front wall being spaced inwardly from the front edges of the top, bottom and sidewalls;
   motor means disposed within said compartment and mounted on said housing means between said front and rear walls, said motor means having a rotatable shaft projecting outwardly from one end thereof and supported by antifriction bearing means on the motor housing;
   a pump housing fixedly mounted relative to said housing means, said pump housing being separate and independent of said housing means and said motor means, said pump housing defining thereon a partially cylindrical wall disposed concentric to the axis of said shaft, said pump housing comprising an annular member secured relative to said front wall and disposed adjacent the outer surface thereof;

cover means hingedly connected to one of the front edges of said housing means and spaced outwardly from said front wall for closing off the front end of said housing means, said cover means and said front wall defining a narrow compartment therebetween in which is positioned said pump housing;

rotor means eccentrically mounted on said shaft radially within and spaced from said partially cylindrical wall, the peripheral surface of said rotor means being rotatable with respect to said shaft and being movable towards, along and then away from said partially cylindrical wall as said shaft is rotated; and elongated resiliently flexible tube means extending along and between the peripheral surface of said rotor means and the adjacent surface of said cylindrical wall whereby said tube means is substantially compressed with a rolling motion during each rotation of said shaft to induce the movement of liquid through said tube means.

4. An apparatus according to claim 3, wherein said tube means comprises a one-piece elongated flexible tube which extends through the pump housing so as to be contacted by said rotor means, the opposite ends of said one-piece tube projecting outwardly from said housing means.

5. An apparatus according to claim 3, wherein said front wall has an enlarged opening formed therein and through which projects said shaft, said pump housing having a rearwardly projecting annular portion which extends through said opening and is seated on said front wall, the rearwardly projecting portion of said pump housing being disposed in abutting engagement with the forward end of the motor housing.

6. An apparatus for effecting a therapeutic lavage, comprising:

housing means defining therein a substantially closed compartment, said housing means including top and bottom walls interconnected by first and second pairs of substantially parallel side walls, the side walls of said first pair extending between and substantially perpendicular to the side walls of said second pair, one of said walls having an opening means formed therein;

motor means disposed within said compartment and mounted on said housing means, said motor means having rotatable shaft means projecting outwardly from one end thereof, said shaft means extending into said opening means;

a pump housing fixedly mounted relative to said housing means, said pump housing comprising a member which is separate and independent of said housing means and said motor means, said pump housing being secured relative to said one wall and disposed adjacent the outer surface thereof, and said pump housing defining thereon a partially cylindrical wall disposed concentric to the axis of said shaft means;

cover means hingedly connected to one of the edges of said housing means and spaced outwardly from said one wall for defining a narrow compartment therebetween in which is positioned said pump housing;

rotor means eccentrically mounted on said shaft means radially within and spaced from said partially cylindrical wall, the peripheral surface of said rotor means being rotatable with respect to said shaft means and being movable toward, along and then away from said partially cylindrical wall as said shaft means is rotated; and elongated resiliently flexible tube means extending along and between the peripheral surface of said rotor means and the adjacent surface of said cylindrical wall whereby said tube means is substantially compressed with a rolling motion during each rotation of said shaft means to induce the movement of liquid through said tube means.

7. An apparatus according to claim 6, wherein said pump housing has an annular mounting portion which extends through said opening means and is seated on said one wall, said annular mounting portion being disposed in abutting engagement with the forward end of the motor housing.

8. An apparatus according to claim 6, wherein said rotor means comprises a single cylindrical roller of substantial diameter, said roller being rotatably supported on said shaft means in eccentric relationship relative to the axis of said shaft means.

9. An apparatus according to claim 6, wherein said pump housing has said partially cylindrical wall formed on one side thereof and has a mounting portion disposed on the other side thereof, said mounting portion projecting into said opening means for seating said pump housing on said one wall, said pump housing also having a small central opening extending therethrough in substantial alignment with the axis defined by said partially cylindrical wall, said shaft means projecting through said central opening, and said shaft means being rotatably supported solely by bearing means mounted on the motor housing.

* * * * *